US00PP37854P2

(12) United States Plant Patent
Bergman

(10) Patent No.: US PP37,854 P2
(45) Date of Patent: Nov. 24, 2026

(54) ***CHRYSANTHEMUM* PLANT NAMED 'CIDZ0129'**

(50) Latin Name: ***Chrysanthemum* x *morifolium***
Varietal Denomination: CIDZ0129

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 9 days.

(21) Appl. No.: 19/651,920

(22) Filed: Apr. 20, 2026

(51) Int. Cl.
*A01H 5/02* (2018.01)

(52) U.S. Cl.
USPC ..... Plt./286

(58) Field of Classification Search
USPC ..... Plt./286
CPC ..... A01H 6/1424; A01H 5/02
See application file for complete search history.

*Primary Examiner* — Keith O. Robinson
(74) *Attorney, Agent, or Firm* — Dale Skalla

(57) ABSTRACT

A new *Chrysanthemum* plant named 'CIDZ0129' particularly distinguished by medium sized white single-type inflorescences, strong and uniform plant habit, dense foliage and a flowering response time of seven weeks.

1 Drawing Sheet

Latin name of the genus and species of the plant claimed: *Chrysanthemum* x *morifolium.*

Varietal denomination: 'CIDZ0129'.

BACKGROUND OF THE NEW PLANT

The present invention comprises a new *Chrysanthemum*, botanically known as *Chrysanthemum* x *morifolium*, and hereinafter referred to by the variety name 'CIDZ0129'.

'CIDZ0129' is a product of a planned breeding program. The new cultivar has medium sized white single-type inflorescences, strong and uniform plant habit, dense foliage and a flowering response time of seven weeks.

'CIDZ0129' originated from a hybridization made in October 2021 in a greenhouse in Enkhuizen, The Netherlands. The female parent was the unpatented, proprietary breeding line designated as 'C1598', having yellow single-type inflorescences, wide branching and more vigorous plant habit when compared to 'CIDZ0129'.

The male parent of 'CIDZ0129' was the unpatented, proprietary breeding line designated as 'C1517', having white single-type inflorescences, compact growth habit, slower flowering response and significantly more pollen production than 'CIDZ0129'.

The seed was sown in August 2022 and the resulting plants were grown out of doors under shade structure in Alva, Florida. 'CIDZ0129' was selected as one flowering plant within the progeny of the stated cross in December 2022.

The first act of asexual reproduction of 'CIDZ0129' was accomplished when vegetative cuttings were propagated from the initial selection in March 2023 in Alva, Florida.

BRIEF SUMMARY OF INVENTION

Horticultural examination of plants grown from cuttings of the plant initiated in March 2023 and continuing thereafter, has demonstrated that the combination of characteristics as herein disclosed for 'CIDZ0129' are firmly fixed and are retained through successive generations of asexual reproduction.

'CIDZ0129' has not been observed under all possible environmental conditions. The phenotype may vary significantly with variations in environment such as temperature, light intensity and day length.

A Plant Breeder's Right for this cultivar has not yet been applied for. 'CIDZ0129' has not been made publicly available prior to the effective filing date of this application, notwithstanding any disclosure that may have been made less than one year prior to the effective filing date of this application by the inventor or another who obtained 'CIDZ0129' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

Figure 1:
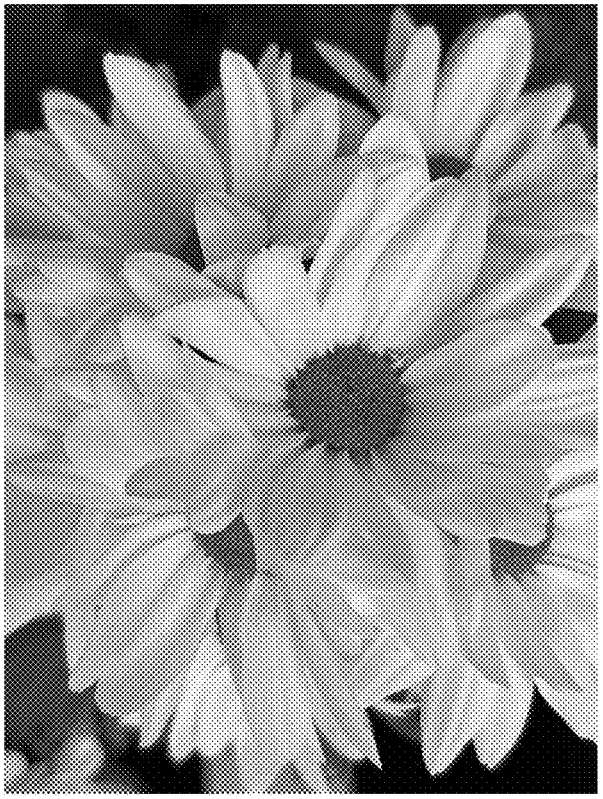
Figure 2:
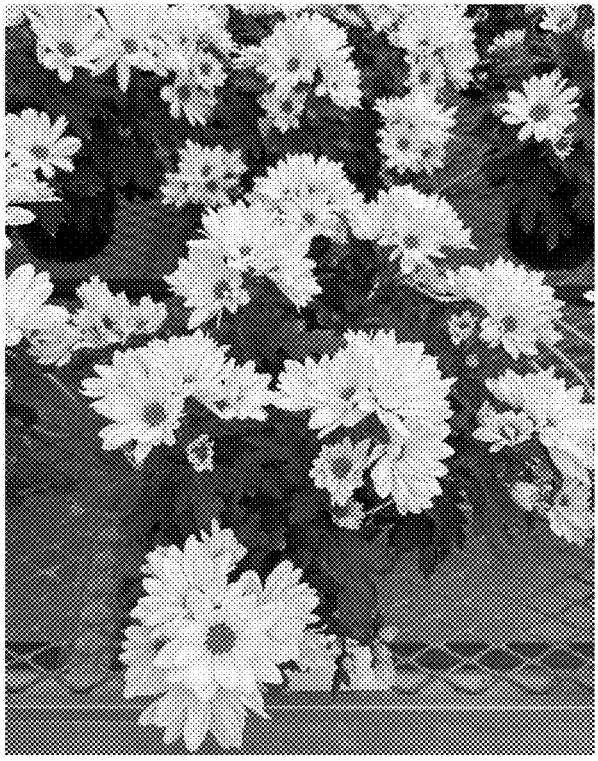

The accompanying photographic drawings show typical flower and foliage characteristics of 'CIDZ0129' with colors being as true as possible with an illustration of this type. The photographic drawings, taken in Gilroy, California in November 2025, show in FIG. 1 a close-up view of the inflorescence of the new variety and in FIG. 2 a whole flowering plant.

DETAILED BOTANICAL DESCRIPTION

The plant descriptions and measurements were taken indoors in Gilroy, California in November 2025 on about 11-week-old plants. Unrooted cuttings had been planted, 4 plants per pot, in 6 inch pots in September 2025. The plants were pinched and moved to short days three weeks later in September 2025 to induce flowering.

Color references are made to The Royal Horticultural Society Colour Chart (R.H.S.) 2001.

TABLE 1

DIFFERENCES BETWEEN THE NEW VARIETY 'CIDZ0129' AND A MOST SIMILAR VARIETY:

| | 'CIDZ0129' | 'CIDZ0090', U.S. Plant Pat. No. 30,029 |
|---|---|---|
| Plant habit: | Shorter | Taller |
| Foliage size: | Larger | Smaller |
| Flowering response: | 2-3 days faster | 2-3 days slower |

Plant:

*Form, growth and habit.*—Herbaceous pot-type, stems upright to moderately angled, freely branching, strong and medium growth habit.

*Plant height.*—15.0 cm.

*Plant height (inflorescence included).*—21.0 cm.

*Plant width.*—34.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage

*Arrangement.*—Alternate.

*Immature, leaf color, upper surface.*—RHS 138A.

*Lower surface.*—RHS 138B.

*Mature, leaf color, upper surface.*—RHS 139A.

*Lower surface.*—RHS 138A.

*Length.*—5.9-7.3 cm.

*Width.*—5.3-7.8 cm.

*Shape.*—Ovate.

*Base shape.*—Attenuate.

*Apex shape.*—Mucronulate.

*Margin.*—Palmately lobed; irregularly incised, somewhat serrate.

*Texture, upper surface.*—Puberulent.

*Lower surface.*—Puberulent.

*Color of veins, upper surface.*—Closest to RHS 138B.

*Color of veins, lower surface.*—RHS 138A.

*Pattern of veining.*—Palmate.

*Petiole color.*—RHS 139A.

*Length.*—2.2-2.9 cm.

*Diameter.*—0.3-0.9 cm.

*Texture.*—Puberulent.

Stem:

*Quantity of main branches per plant.*—3-4.

*Color of stem.*—RHS 138B.

*Length of stem.*—10.0-11.0 cm.

*Diameter.*—0.4-0.6 cm.

*Length of internodes.*—0.3-1.3 cm.

*Texture.*—Puberulent.

*Color of peduncle.*—RHS 138A.

*Length of peduncle.*—2.6-5.2 cm.

*Peduncle diameter.*—0.25 cm.

*Texture.*—Puberulent.

Inflorescence:

*Type.*—Compositae type, single-type inflorescences borne terminally above foliage, ray florets arranged acropetally on a capitulum.

*Quantity of short days to flowering (response time).*—7 weeks.

*Natural season flowering.*—Not determined for this variety.

*Quantity of inflorescences per plant.*—17-22.

*Lastingness of individual blooms on the plant.*—4 weeks.

*Fragrance.*—Slightly spicy.

Bud (just when opening/showing color):

*Color.*—Closest to RHS 149D.

*Length.*—1.2 cm.

*Width.*—1.2 cm.

*Shape.*—Oblate.

Immature inflorescence:

*Diameter.*—4.6-5.1 cm.

*Color of ray florets, upper surface.*—RHS 155D.

*Lower surface.*—RHS 155D.

Mature inflorescence:

*Diameter.*—7.1-7.8 cm.

*Depth.*—2.4 cm.

*Total diameter of disc.*—1.4 cm.

*Receptacle color.*—RHS 145B.

*Receptacle height.*—0.55 cm.

*Receptacle diameter.*—0.7 cm.

Ray florets:

*Average quantity of florets.*—28.

*Color of florets, upper surface.*—RHS 155D.

*Lower surface.*—RHS 155D.

*Length.*—2.5-3.4 cm.

*Width.*—0.9-1.1 cm.

*Shape.*—Elliptical.

*Apex shape.*—Irregularly apiculate.

*Margin.*—Entire.

*Texture, upper surface.*—Papillose.

*Lower surface.*—Papillose.

Disc florets:

*Average quantity of florets.*—202.

*Color of florets.*—Apex RHS 149C, midpoint RHS 1A.

*Length.*—0.45 cm.

*Width.*—0.1 cm.

*Shape.*—Tubular, elongated.

*Apex shape.*—Acute, 5 pointed.

Phyllaries:

*Quantity.*—Average 25.

*Color, upper surface.*—RHS 1397B.

*Lower surface.*—RHS 137C.

*Length.*—0.5-0.6 cm.

*Width.*—0.2 cm.

*Shape.*—Lanceolate

*Apex shape.*—Acute.

*Base.*—Fused.

*Margins.*—Entire; slightly papery.

*Texture, upper surface.*—Glabrous.

*Lower surface.*—Puberulent.

Reproductive organs:

*Pistil.*—1, found on both types of florets.

*Length.*—0.5 cm.

*Style color.*—RHS 150D.

*Style length.*—0.4 cm.

*Stigma color.*—RHS 4B.

*Stigma shape.*—Bi-parted.

*Ovary color.*—RHS 155C but more translucent.

*Stamens.*—4, found on only on the disc florets.

*Color of filaments.*—RHS 155C.

*Length filaments.*—0.2 cm.

*Anther color.*—RHS 12A.

*Anther length.*—0.15 cm.

*Anther shape*.—Oval.
*Color of pollen*.—RHS 13A.
*Pollen amount*.—Very little.
*Fertility/seed set*.—Has not been determined.
*Disease/pest resistance*.—Has not been observed to date.

What is claimed is:

1. A new and distinct variety of *Chrysanthemum* plant named 'CIDZ0129' substantially as illustrated and described herein.

* * * * *